United States Patent
Straszheim-Morley et al.

(10) Patent No.: US 7,850,698 B2
(45) Date of Patent: Dec. 14, 2010

(54) TIBIAL TRIALING ASSEMBLY AND METHOD OF TRIALING A TIBIAL IMPLANT

(75) Inventors: Kristina J. Straszheim-Morley, Warsaw, IN (US); Dwight T. Todd, Columbia City, IN (US); Brian D. Byrd, North Webster, IN (US); Scott C. Lazar, Cromwell, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 0 days.

(21) Appl. No.: 12/542,273

(22) Filed: Aug. 17, 2009

(65) Prior Publication Data

US 2010/0010635 A1    Jan. 14, 2010

Related U.S. Application Data

(62) Division of application No. 11/348,990, filed on Feb. 7, 2006, now abandoned.

(60) Provisional application No. 60/653,902, filed on Feb. 17, 2005.

(51) Int. Cl.
*A61B 17/58* (2006.01)
*A61B 17/60* (2006.01)
*A61F 5/04* (2006.01)
*A61F 2/42* (2006.01)

(52) U.S. Cl. .................. 606/102; 606/86 R; 606/88; 623/20.14

(58) Field of Classification Search ............... 606/86 R, 606/87, 88, 102; 623/20.14
See application file for complete search history.

(56) References Cited

U.S. PATENT DOCUMENTS

| | | | |
|---|---|---|---|
| 2,638,092 A | 5/1953 | Dorr | |
| 4,646,729 A | 3/1987 | Kenna et al. | |
| 4,738,254 A | 4/1988 | Buechel et al. | |
| 4,950,271 A | 8/1990 | Lewis et al. | |
| 5,116,338 A | 5/1992 | Poggie et al. | |
| 5,250,050 A | 10/1993 | Poggie et al. | |
| 5,306,276 A | 4/1994 | Johnson et al. | |
| 5,445,640 A | 8/1995 | Johnson et al. | |

(Continued)

OTHER PUBLICATIONS

Nexgen Complete Knee Solution Surgical Technique for Legacy Posterior Stabilized Knees, pp. 1-44, Catalog No. 97-5996-002 00 Rev. 2002, 2008 Zimmer, Inc.

*Primary Examiner*—Eduardo C Robert
*Assistant Examiner*—Ellen C Hammond
(74) *Attorney, Agent, or Firm*—Baker & Daniels LLP

(57) ABSTRACT

A trialing assembly for use during knee replacement procedures to determine size and position of a tibial plate implant as well as the size and thickness of the articular surface prior to implantation of the implant. The trialing assembly includes a broaching plate having a tibia engaging bottom surface adapted for placement atop a tibia and an opposite top surface, the bottom and top surfaces extending between an anterior edge and a posterior edge of the broaching plate. The broaching plate includes an anterior rail and a posterior rail protruding superiorly from the top surface and extending along the anterior and posterior edges, respectively. A trialing plate is configured to removably fit atop the broaching plate between the anterior and posterior rails. The trialing plate includes an engagement member extending from a superior surface of the trialing plate and adapted to engage with an articular surface provisional.

31 Claims, 13 Drawing Sheets

U.S. PATENT DOCUMENTS

| | | | |
|---|---|---|---|
| 5,609,642 A * | 3/1997 | Johnson et al. | 606/88 |
| 5,611,802 A | 3/1997 | Samuelson et al. | |
| 5,658,292 A | 8/1997 | Axelson, Jr. | |
| 5,693,056 A | 12/1997 | Carls et al. | |
| 5,702,463 A * | 12/1997 | Pothier et al. | 623/20.32 |
| 5,702,464 A * | 12/1997 | Lackey et al. | 623/20.32 |
| 5,733,290 A | 3/1998 | McCue et al. | |
| 5,908,424 A | 6/1999 | Bertin et al. | |
| 5,989,261 A | 11/1999 | Walker et al. | |
| 6,063,091 A * | 5/2000 | Lombardo et al. | 606/88 |
| 6,214,052 B1 * | 4/2001 | Burkinshaw | 623/20.34 |
| 6,344,043 B1 | 2/2002 | Pappas | |
| 6,423,073 B2 | 7/2002 | Bowman | |
| 6,645,215 B1 | 11/2003 | McGovern et al. | |
| 6,692,503 B2 | 2/2004 | Foley et al. | |
| 6,942,670 B2 * | 9/2005 | Heldreth et al. | 606/102 |
| 2002/0082607 A1 * | 6/2002 | Heldreth et al. | 606/102 |
| 2006/0064108 A1 | 3/2006 | Blaylock et al. | |

* cited by examiner

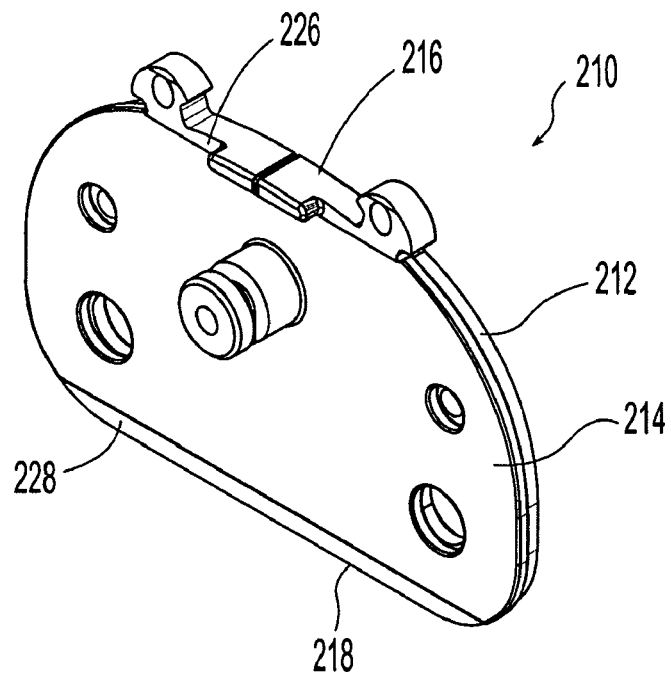
Fig. 8
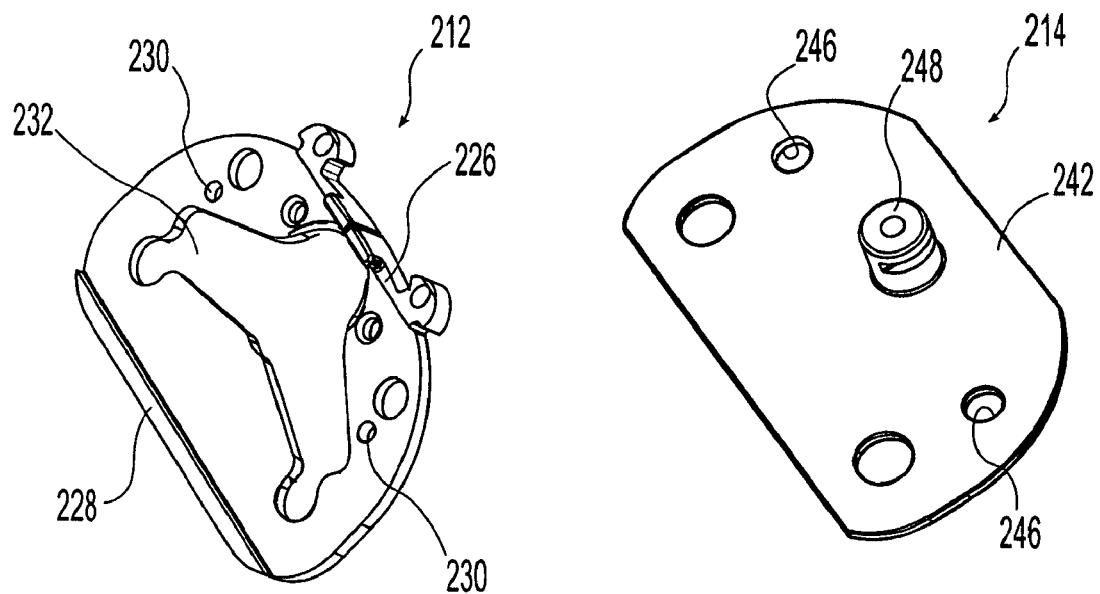
Fig. 9
Fig. 10

TIBIAL TRIALING ASSEMBLY AND METHOD OF TRIALING A TIBIAL IMPLANT

PRIORITY REFERENCE

This application is a Divisional of U.S. patent application Ser. No. 11/348,990, entitled TIBIAL TRAILING ASSEMBLY AND METHOD OF TRAILING A TIBIAL IMPLANT, filed Feb. 7, 2006, now abandoned, which claims priority to U.S. provisional application Ser. No. 60/653,902, filed in the name of Kristina J. Morley et al. on Feb. 17, 2005, and entitled TIBIAL TRIALING ASSEMBLY AND METHOD OF TRIALING A TIBIAL IMPLANT, the entire disclosures of which are expressly incorporated by reference herein.

BACKGROUND

The present invention relates to trialing devices used during knee replacement procedures to size and prepare a resected tibia for receiving a tibial implant and to evaluate the stability and kinematic performance of the articular surface provisional prior to implantation of the tibial implant.

Generally, the knee is the joint between the femur and the tibia. The knee joint is formed of a pair of condyles located at the distal portion of the femur, a tibial plateau located at the proximal end of the tibia and shaped to mate with the pair of condyles, and a pair of menisci positioned between the tibial plateau and the condyles. The femur and the tibia are connected by ligaments, which provide stability to the knee. Such ligaments include the posterior cruciate ligament (PCL), the lateral collateral ligament, the medial collateral ligament, and the anterior cruciate ligament. Significant disease of, or trauma to, the knee may warrant replacement of the knee with a prosthetic knee (knee implant).

A prosthetic total knee joint generally includes a femoral component and a tibial component. The tibial component typically includes a tibial tray or plate and a prosthetic bearing insert. The tibial tray often includes a stem, which extends from the bottom of the tray and is sized for insertion into the tibia. In some knee implants, the bearing insert may be fixed to the tibial tray such that the bearing insert is immobile relative to the tibial tray. These knee implant designs are often referred to as "fixed bearing" designs. In other knee implants, the bearing insert is movably fixed to the tibial tray thereby allowing the bearing insert to move relative to the tibial tray. These knee implant designs are typically referred to as "mobile bearing" designs.

During mobile bearing knee replacement surgery, the surgeon first prepares the proximal end of the tibia by resecting the proximal tibia or, in the case of revision, removing the damaged tibial components prior to resecting the proximal tibia. After the tibia is prepared, a tibial sizing plate is aligned and placed on the resected tibia, and checked for size. After the proper sizing plate is selected and the optimal location is determined, the sizing plate is fixed in position on the resected tibia by inserting pins through the sizing plate and into the resected tibia. The pins generally have cap heads that remain extended above the surface of the sizing plate so that the pins can be extracted upon completion of the trial. Next, the surgeon selects an articular surface provisional, which is modeled in shape and design after the bearing insert of the tibial component that the surgeon proposes to implant. The surface provisional is then engaged with the sizing plate. With the articular surface provisional in place, the surgeon then performs trialing procedures to test the fit and function of the articular surface provisional. Such trialing procedures may include measuring the flexion and extension gaps, and conducting range of motion tests, during which the anterior/posterior and medial/lateral stability and movement may be tested. These trialing procedures help the surgeon determine the proper sized bearing insert. The surgeon may repeat the trialing procedures with different sized provisionals until the desired results are achieved.

Next, the surgeon removes the pins and the sizing plate. A broaching plate is then positioned and carefully aligned on the resected tibia such that pin holes in the broaching plate are aligned with the pin holes created in the tibia by the mounting of the sizing plate. Once aligned, the broaching plate is pinned in place. With the broaching plate in place, a drill/broach guide is engaged with the upper surface of the broaching plate and the proximal tibia is drilled and/or broached to accommodate the tibial stem of the tibial tray.

There is a need for a tibial trialing device that simplifies and minimizes the steps of knee replacement surgery.

SUMMARY

The present invention provides a trialing assembly for use during knee replacement procedures to prepare and size a resected tibia for receiving a tibial implant and to evaluate the stability and kinematic performance of the articular surface provisional prior to implantation of the tibial implant. In one form, the trialing assembly includes a broaching plate having an outer periphery substantially conforming to the resected tibia. The broaching plate includes a bottom surface adapted for placement atop the resected tibia and an opposite top surface. The bottom and top surfaces extend substantially between the outer periphery. The broaching plate includes a plurality of alignment rails protruding superiorly from the top surface and extending along at least a portion of the outer periphery. A trialing plate is configured to removably fit atop the broaching plate between the plurality of alignment rails. The trialing plate has a superior surface and a boss extending superiorly from the superior surface. The boss is adapted to engage with an articular surface provisional.

In another form, the trialing assembly includes a broaching plate having an outer periphery, a bottom surface adapted for placement atop the resected tibia and an opposite top surface. The bottom and top surfaces extend substantially between the outer periphery. A trialing plate is removably disposed atop the broaching plate and overlies substantially all of the top surface. The trialing plate includes a boss extending superiorly from the superior surface of the trialing plate. The boss is adapted to engage with the articular surface provisional.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 8 is a perspective view of a tibial trialing assembly according to another embodiment of the present invention;

FIG. 9 is a perspective view of the broaching plate of the tibial trialing assembly of FIG. 8;

FIG. 10 is a perspective view of the trialing plate of the tibial trialing assembly of FIG. 9;

Figure 1:
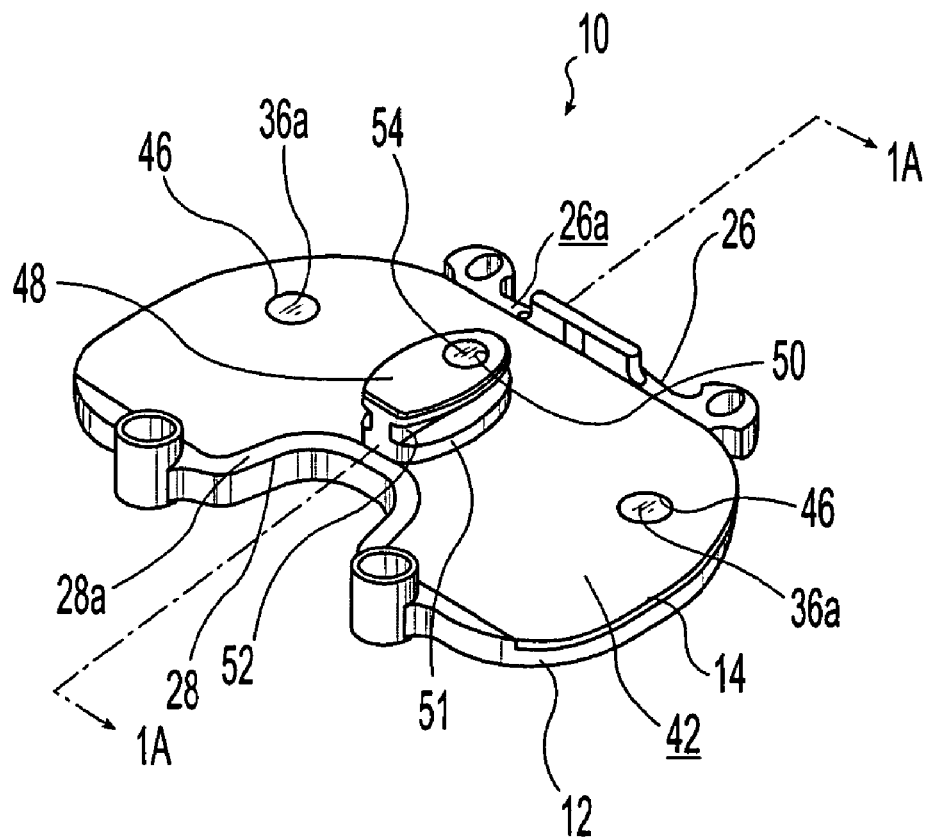
FIG. 1 is a perspective view of a tibial trialing assembly according to one embodiment of the present invention.

Corresponding reference characters indicate corresponding parts throughout the several views. Although the drawings represent embodiments of the present invention, the drawings are not necessarily to scale and certain features may be exaggerated in order to better illustrate and explain the present invention. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The present invention will now be described with reference to the attached figures. The description below may include references to the following terms: anterior (at or near the front of the body, as opposed to the back of the body); posterior (at or near the back of the body, as opposed to the front of the body); lateral (at or near the side of the body, farther from the midsagittal plane, as opposed to medial); medial (at or near the middle of the body, at or near the midsagittal plane, as opposed to lateral); proximal (toward the beginning, at or near the head of the body, as opposed to distal) and distal (further from the beginning, at or near the foot of the body, as opposed to proximal).

Figure 1A:
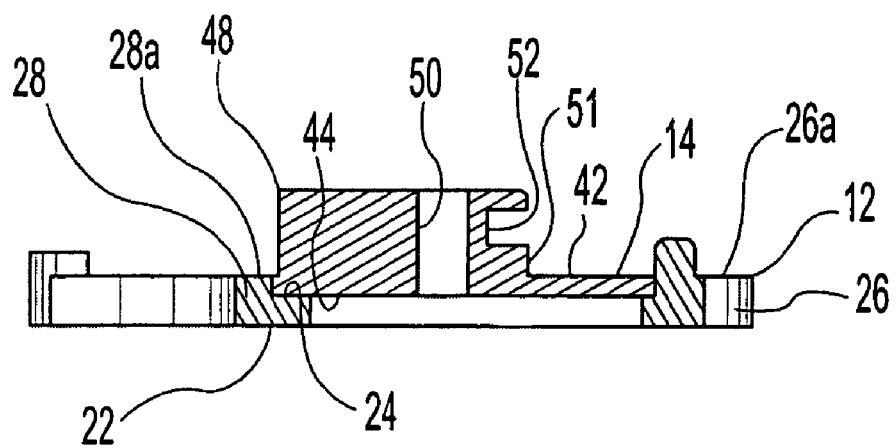
FIG. 1A is a sectional view of the tibial trialing assembly taken along line 1A-1A of FIG. 1.
Figure 2:
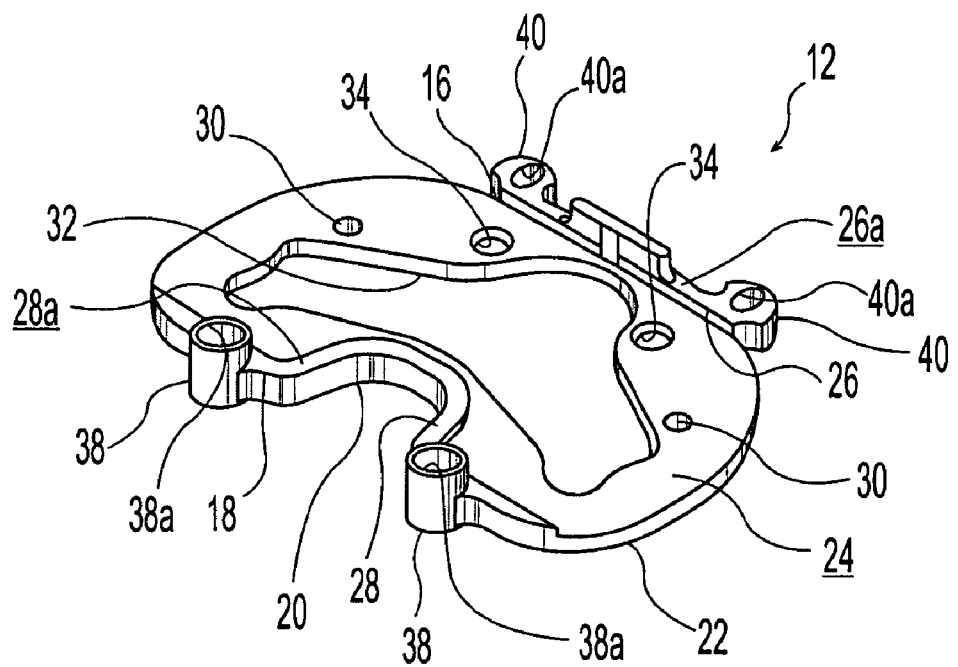
FIG. 2 is a perspective view of the broaching plate of the tibial trialing assembly of FIG. 1.

Referring first to FIG. 1, tibial trialing assembly 10 according to one embodiment of the present invention is shown. Trialing assembly 10 generally includes broaching plate 12 and trialing plate 14. Referring now to FIGS. 1, 1A and 2, broaching plate 12 includes an outer periphery shaped to conform to a resected tibia. The outer periphery includes anterior edge 16 and opposing posterior edge 18. Broaching plate 12 also includes bottom surface 22 and opposing top surface 24. Bottom and top surfaces 22, 24 are substantially flat and extend between anterior edge 16 and posterior edge 18. As is discussed in further detail below, broaching plate 12 is sized for placement atop a resected tibia. Accordingly, bottom surface 22 is configured for placement on, and contact with, the resected tibia. In addition, a portion of posterior edge 18 curves inward toward anterior edge 16 to form PCL cutout 20. PCL cutout 20 is configured to accommodate the patient's posterior cruciate ligament when broaching plate 12 is placed atop the resected tibia.

Referring still to FIGS. 1 and 2, broaching plate 12 includes a pair of opposing alignment rails 26, 28 protruding superiorly from top surface 24. Pair of opposing alignment rails 26, 28 includes anterior rail 26, which extends along a portion of anterior edge 16. Posterior rail 28 extends along a portion of posterior edge 18. Particularly, posterior rail 28 extends along and around PCL cutout 20 of posterior edge 18. Anterior rail 26 and posterior rail 28 include superior surfaces 26a, 28a, respectively.

Referring now to FIG. 2, pin holes 30 extend through broaching plate 12 from top surface 24 to bottom surface 22. Pin holes 30 are adapted to receive pins 36 (FIG. 4) or any other fasteners including screws or nails, as further discussed below. Broaching plate 12 includes broach receiving opening 32 extending through broaching plate 12. As discussed in further detail below, broach receiving opening 32 is sized and configured to allow the passage of a drill and/or a broach. Alignment openings 34 extend through broaching plate 12 and are adapted to receive alignment pegs 64 (FIG. 6) of broach impactor and/or drill guide 60 (FIG. 6), as is discussed in further detail below.

Referring to FIGS. 1 and 2, broaching plate 12 includes anterior tabs 40 protruding anteriorly from anterior edge 16. Anterior tabs 40 define openings 40a which together with tabs 40 are adapted to engage with a handle (not shown) to facilitate the positioning of broaching plate 12 on the resected tibia, as described in U.S. patent application Ser. No. 10/938,979, entitled Tibial Sizing Apparatus and Method filed Sep. 9, 2004, assigned to the assignee of the present application and hereby incorporated by reference. Broaching plate 12 further includes posterior tabs 38 extending posteriorly from posterior edge 18. Posterior tabs 38 define openings 38a, which are configured to receive drop down screws (not shown). Posterior tabs 38, openings 38a, and drop down screws cooperate, as described in the above-incorporated U.S. patent application Ser. No. 10/938,979, to further aid in the positioning of broaching plate 12 on the resected tibia.

Broaching plate 12 may be formed of any surgical grade rigid material. For example, broaching plate 12 may be formed of cobalt chromium, stainless steel, titanium, and/or alloys thereof. Broaching plate 12 may be made available in various sizes to accommodate various sized tibias.

Figure 3:
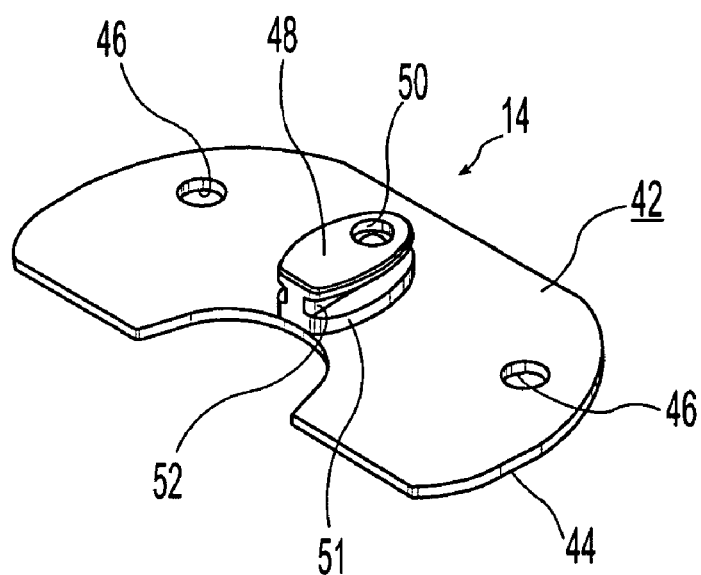
FIG. 3 is a perspective view of the trialing plate of the tibial trialing assembly of FIG. 1.

Turning now to FIGS. 1 and 3, trialing plate 14 includes substantially flat superior surface 42 and substantially flat, opposing inferior surface 44. Head receiving openings 46 extend through trialing plate 14 from superior surface 42 to inferior surface 44 and are adapted to accommodate head 36a of pins 36 (FIG. 4), as further discussed below.

Trialing plate 14 includes articular surface provisional engagement member or boss 48 protruding superiorly from superior surface 42. As discussed below, boss 48 has an elliptically shaped cross-section and is configured to engage with an articular surface provisional. Alternatively, engagement member or boss 48 may have a variety of shapes and sizes to accommodate engagement with various designs of surface provisionals. Furthermore, trialing plate may comprise more than one articular surface provisional engagement member or boss. Central bore 50 extends in the superior/inferior direction through boss 48 and trialing plate 14. Bore 50 is adapted to allow the passage of fastener 54 (FIG. 4), as further discussed below. Boss 48 is defined by outer perimetrical wall 51, and includes a trialing plate removal element, which in this embodiment is in the form of groove 52 cut into wall 51. Similar to broaching plate 12, trialing plate 14 may be formed of any surgical grade rigid material. For instance, trialing plate 14 may be formed of cobalt chromium, titanium, stainless steel and/or alloys thereof.

Figure 5:
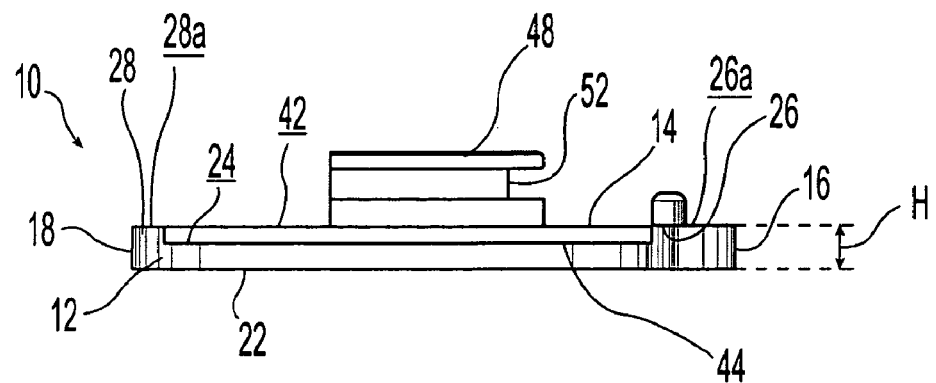
FIG. 5 is a side view of the tibial trialing assembly of FIG. 1.

Turning now to FIGS. 1-3 and 5, trialing plate 14 is sized and configured to removably fit atop broaching plate 12 between anterior and posterior rails 26, 28. When trialing plate 14 is so positioned atop broaching plate 12, trialing plate 14 overlies substantially all of top surface 24 of broaching plate 12. In addition, as illustrated in FIGS. 1A and 5, when trialing plate 14 is properly positioned atop broaching plate 12, superior surface 42 of trialing plate 14 is substantially level, or flush, with superior surfaces 26a and 28a of respective anterior and posterior rails 26, 28 to provide a smooth surface on which the articular surface provisional can move. As shown in FIGS. 1A and 5, when trialing plate 14 is positioned atop broaching plate 12, inferior surface 44 of trialing plate 14 is supported on top surface 24 of broaching plate 12 such that inferior surface 44 is non-level with bottom surface 22. Referring specifically to FIG. 5, when assembled, trialing assembly has height H extending from level superior surfaces 26a, 28a, 42 to bottom surface 22. Height H is sized to correspond to the height of the tibial tray of the tibial implant to be installed.

Figure 4:
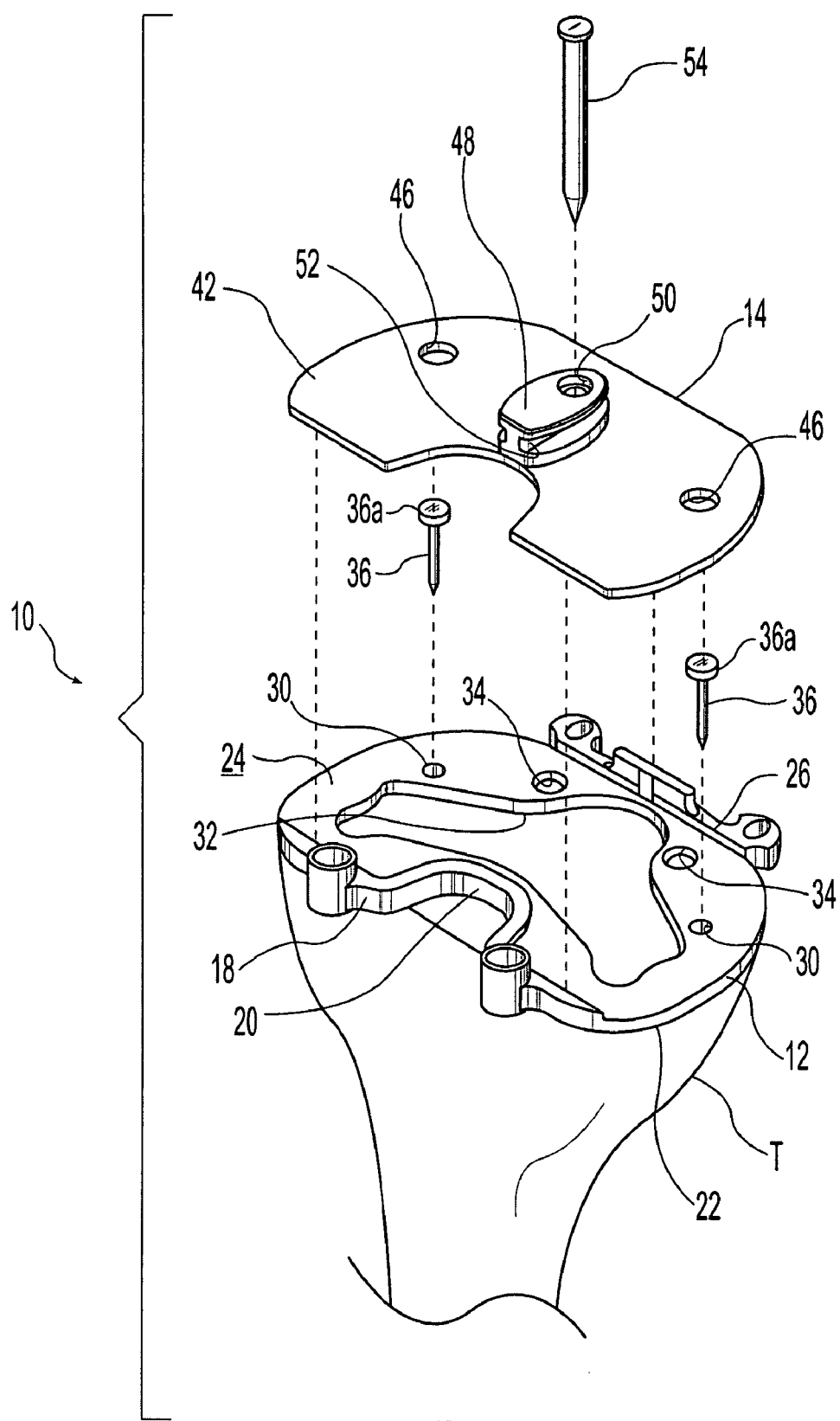
FIG. 4 is an exploded perspective view of the tibial trialing assembly fitted onto a resected tibia.

Turning now to FIG. 4, use of tibial trialing assembly 10 will now be described. After resecting the patient's tibia T, the surgeon selects a tibial trialing assembly 10 that most closely corresponds in size to the proximal surface of tibia T. As noted above, this trialing assembly 10 will have a width equal to the tibial tray of the tibial implant the surgeon proposes to use. Next, broaching plate 12 of trialing assembly 10 is placed on the resected surface of tibia T. Broaching plate 12 is then secured in position on tibia T by inserting pins 36 through pin holes 30 of broaching plate 12 and into tibia T. Heads 36a of pins 36 protrude superiorly from holes 30 such that pins 36 may be easily removed later. Referring now to FIGS. 1, 1A and 4, once broaching plate 12 is secured to tibia T, trialing plate 14 is positioned atop broaching plate 12 between anterior and posterior rails 26, 28. In this position, head receiving openings 46 of trialing plate 14 are aligned with pin holes 30 of broaching plate 12. Protruding heads 36a of pins 36 are received in head receiving openings 46 thereby preventing heads 36a from interfering with the flush placement of inferior surface 44 of trialing plate 14 against top surface 24 of broaching plate 12.

When trialing plate 14 is properly positioned atop broaching plate 12, trialing plate 14 overlies substantially all of top surface 24 of broaching plate 12 to provide a smooth, uninterrupted surface on which the surface provisional may articulate. Once trialing plate 14 is flushly positioned atop broaching plate 12, anterior and posterior rails 26, 28 cooperate to prevent the movement of trialing plate 14 along the plane of top surface 24 in the medial/lateral and anterior/posterior directions. Furthermore, as illustrated in FIGS. 1, 1A, 4 and 5, when in position atop broaching plate 12, superior surface 42 of trialing plate 14 is level with superior surfaces 26a, 28a of respective anterior and posterior rails 26, 28. As illustrated in FIGS. 1A and 5, inferior surface 44 of trialing plate 14 is supported by top surface 24 of broaching plate 12 and, therefore, is spaced apart from bottom surface 22 of broaching plate 12. Trialing plate 14 may be secured in position by driving fastener 54 through bore 50 and into resected tibia T.

Referring now to FIG. 4, a selected articular surface provisional (not shown) may now be engaged with boss 48 and conventional trialing and sizing procedures may be performed. Boss 48 is configured to provide an axis of rotation for trialing articular surface provisionals modeled after mobile bearing implant designs. The surgeon may trial several different sized articular surface provisionals. Once the surgeon has completed the trialing and sizing procedures and has determined the proper size of bearing insert, trialing plate 14 is removed by engaging groove 52 of boss 48 with a tool and pulling trialing plate 14 and fastener 54 from tibia T, exposing broaching plate 12 still aligned and in place on tibia T. The combined height H of broaching plate 12 and trialing plate 14 is substantially equivalent to the tibial plate implant height to mimic the function of the tibial plate during trialing of a selected surface provisional. However, it should be noted that in some cases the combined height H need not be equivalent to the height of the tibial plate. For instance, if the selected articular surface provisional is configured to have a height (thickness) greater than that of the articular surface implant, combined height H may be thinner than the height of the tibial plate. Conversely, if the selected articular surface provisional is configured to have a height (thickness) less than that of the articular surface implant, combined height H may be greater than the height of the tibial plate. In other words, the combined height of the trialing assembly and the articular surface provisional is equivalent to the combined height of the tibial plate implant and the articular surface implant.

Figure 6:
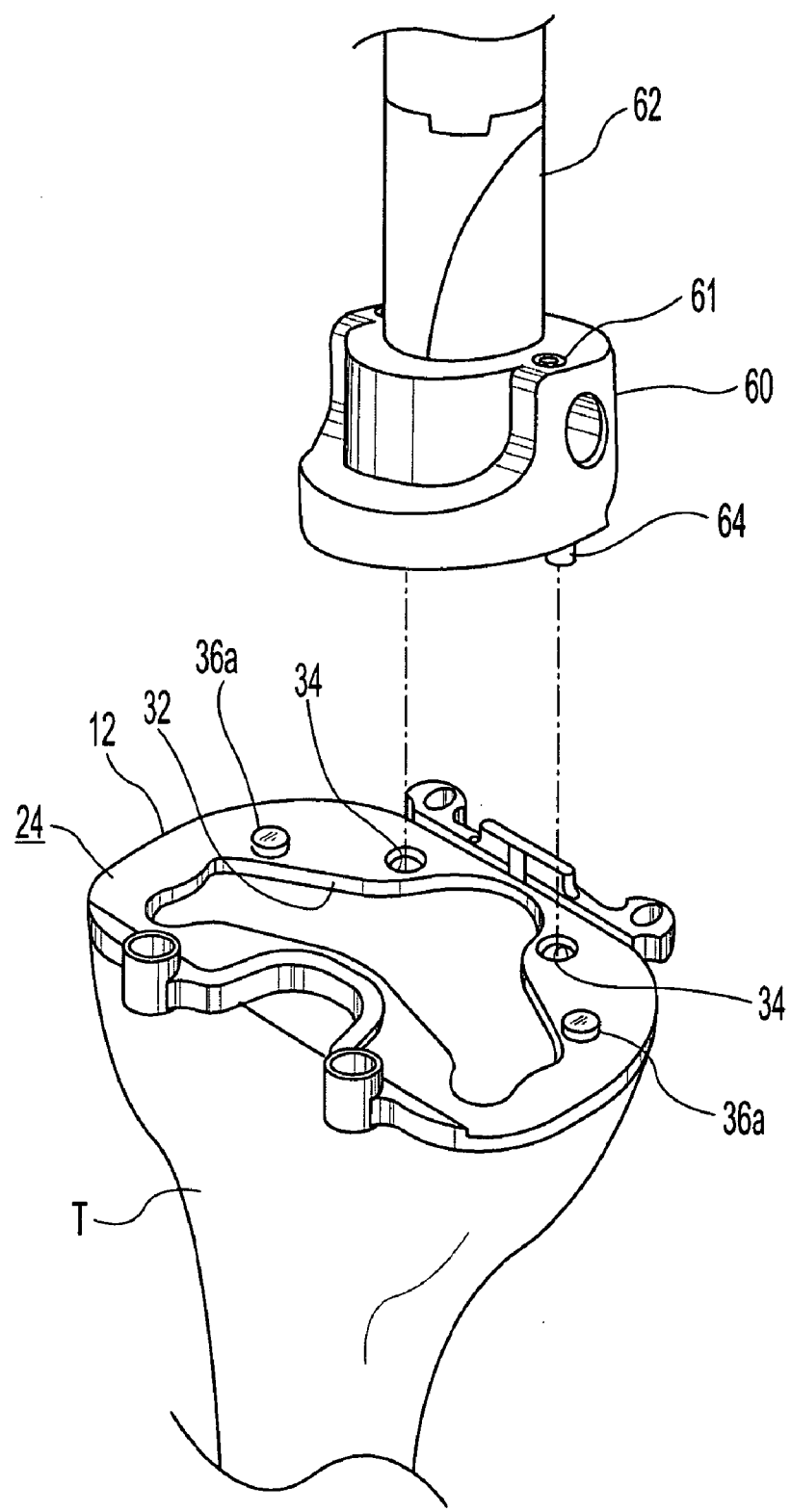
FIG. 6 is an exploded perspective view of the broaching plate of the tibial trialing assembly of FIG. 1 fitted onto a resected tibia and cooperating with a drill and drill guide.

Turning now to FIG. 6, the surgeon can now prepare the tibia for receiving the stem of the tibial tray. The surgeon inserts alignment pegs 64 of drill guide 60 into alignment openings 34. Drill 62 may then be driven through guide 60, then through broach opening 32 and into tibia T to create a passage in tibia T for the acceptance of the stem of the tibial tray. Drill 62 and guide 60 are then removed. Finally, broaching plate 12 is then removed, leaving the prepared, resected tibia ready to receive the tibial tray.

Figure 7:
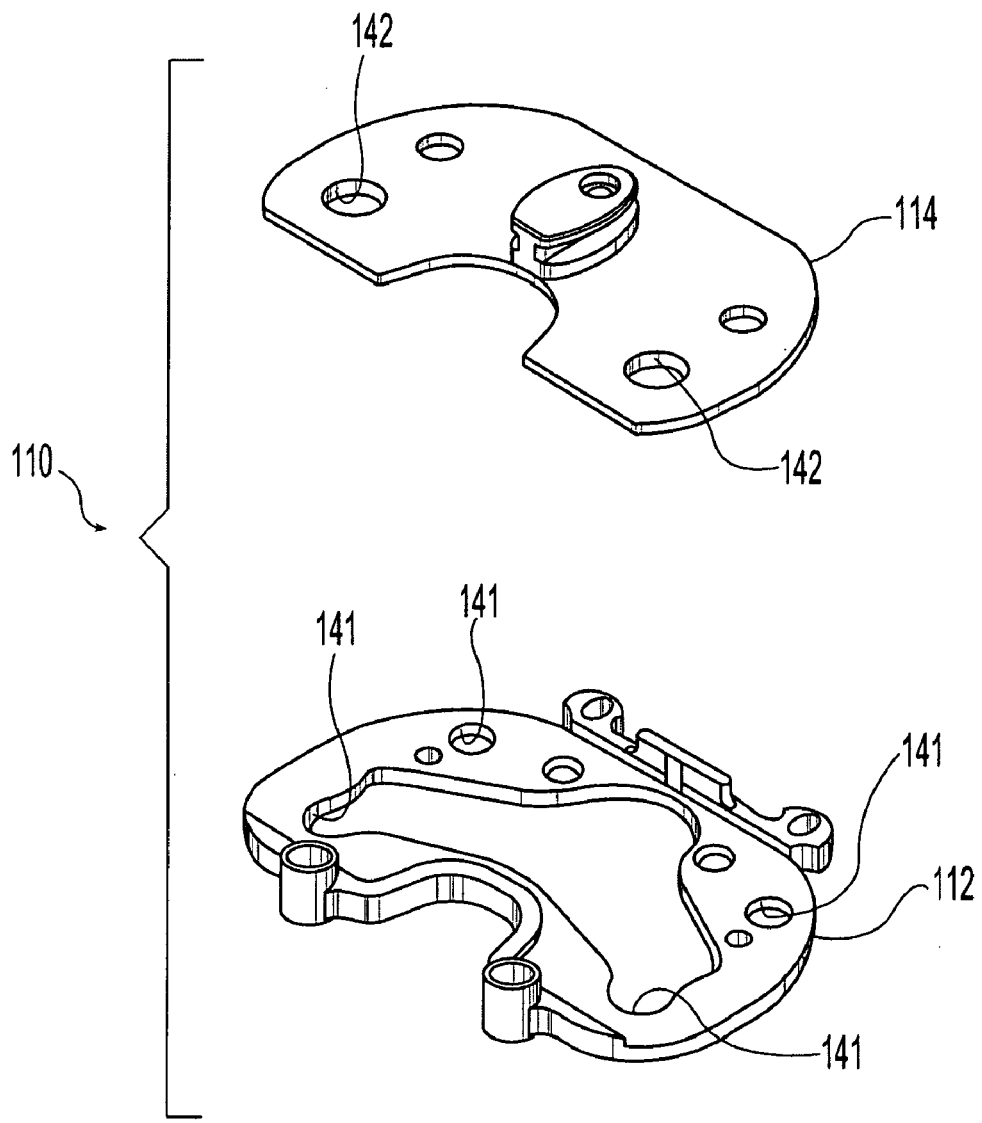
FIG. 7 is a perspective view of a disassembled tibial trialing assembly according to another embodiment of the present invention.

Turning now to FIG. 7, another embodiment is illustrated. Tibial trialing assembly 110 includes broaching plate 112 and trialing plate 114. Broaching plate 112 includes all of the features of broaching plate 12 (FIG. 2) with the addition of augment holes 141. Trialing plate 114 includes all of the features of trialing plate 14 (FIG. 3) with the addition of augment holes 142. Augment holes 141 and 142 are adapted to receive an alignment fastener (not shown) for attaching conventional augment provisionals to trialing assembly 110. Exemplary augment provisionals that may be used with broaching plate 112 include NEXGEN® augment provisionals by Zimmer, Inc. of Warsaw, Ind.

Referring now to FIGS. 8-11, tibial trialing assembly 210 according to another embodiment is illustrated. Tibial trialing assembly 210 includes broaching plate 212 and trialing plate 214. As shown in FIGS. 8 and 9, broaching plate 212 includes an outer periphery shaped to conform to a resected tibia. The outer periphery includes anterior edge 216 and posterior edge 218. Unlike broaching plate 12 of trialing assembly 10 (FIG. 1), posterior edge 218 does not include a PCL cut out portion. Broaching plate 212 includes a pair of opposing alignment rails 226, 228 protruding superiorly from the top surface of broaching plate 212. Pair of opposing alignment rails 226, 228 includes anterior rail 226, which extend along a portion of anterior edge 216, and posterior rail 228, which extends along a portion of posterior edge 218. Pin holes 230 extend through broaching plate 212 and are adapted to receive fasteners (such as pins 36 in FIG. 4) for securing broaching plate 212 to the tibia. Broaching plate 212 also includes broach opening 232, which is sized and configured to allow the passage of a drill and/or broach.

Figure 11:
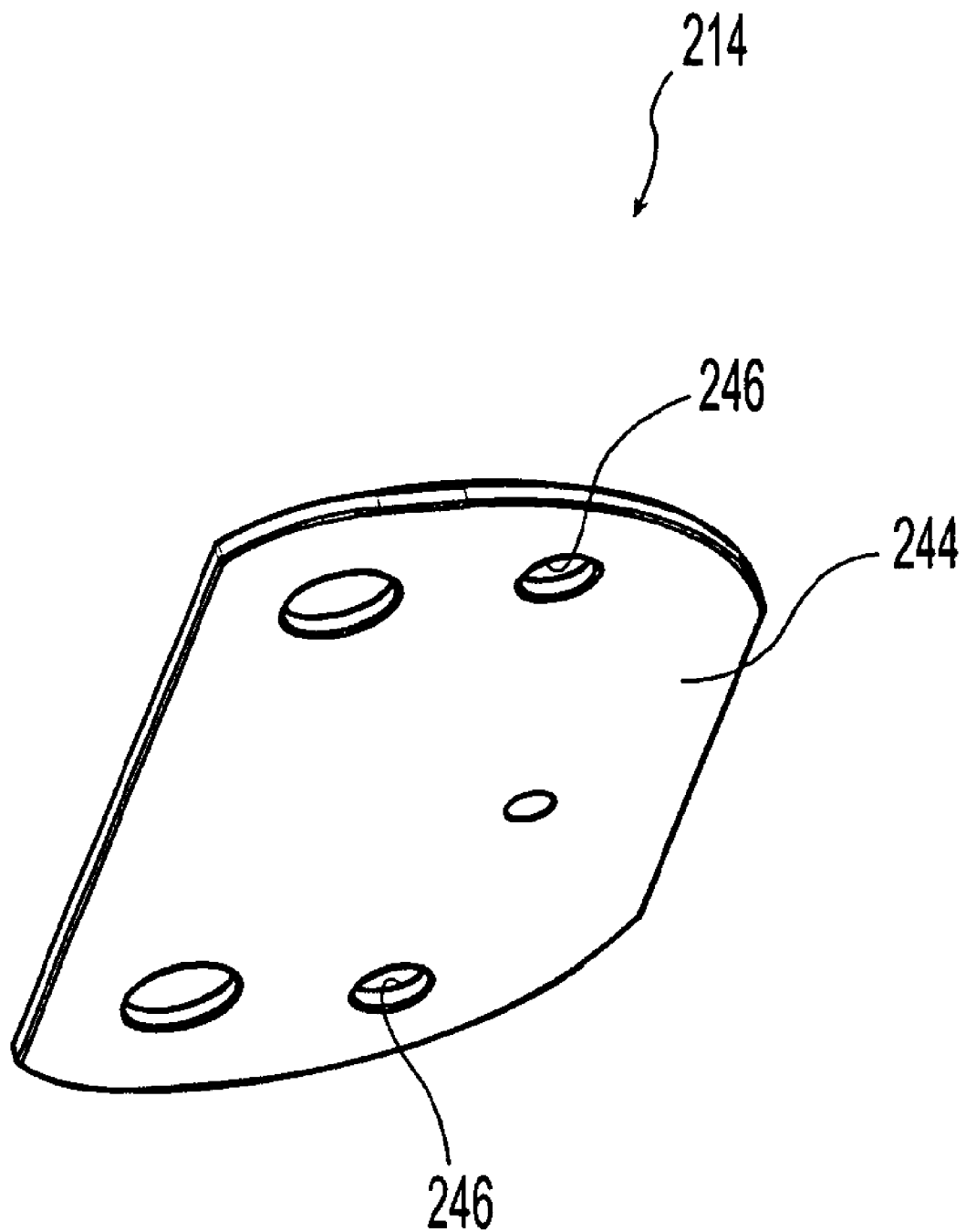
FIG. 11 is another perspective view of the trialing plate of FIG. 10.

Turning now to FIGS. 8, 10 and 11, trialing plate 214 is substantially flat and is sized to fit over broaching plate 212 between anterior and posterior rails 226, 228. Trialing plate 214 includes superior surface 242 and opposing inferior surface 244. Pin head receiving openings 246 extend through trialing plate 214 from superior surface 242 to opposing inferior surface 244. Openings 246 are adapted to accommodate the head of fasteners received within holes 230 of broaching plate 212. Trialing plate 214 includes engagement member or boss 248 protruding superiorly from superior surface 242. As noted above, the boss may have a variety of shapes and sizes. For instance, in the present embodiment, boss 248 has a circular cross-sectional shape, thereby demonstrating at least one alternative shape.

Although the embodiments discussed above show a pair of opposing anterior and posterior rails, alignment rails could, alternatively, include any number of rails positioned at any location along the outer periphery. For instance, the alignment rails may include two opposing rails, one located at the medial edge of the outer periphery and the other at the lateral edge of the outer periphery. In another example, the alignment rails may include three rails spaced apart along the outer periphery. In fact, it is possible to have a single rail extending along a portion of the periphery enough to limit the movement of the trialing plate when mounted atop the broaching plate. Furthermore, the alignment rail or rails need not be positioned on the periphery of the plate. It is also possible to have no alignment rails, instead using alignment members, such as pegs extending from one of the trialing plate or broaching plate and mating with alignment holes in the other of the trialing plate and broaching plate. Alternatively, the pin heads used to fix the broaching plate to the tibia could be used in conjunction with the head receiving openings in the trialing plate to align the trialing plate on the broaching plate. It should also be noted that the alignment rails could be alternatively disposed on the inferior surface of the trialing plate and could engage the outer periphery of the broaching plate such that broaching plate is positioned between the alignment rails of the trialing plate.

For example, FIGS. 12-15 illustrate an embodiment having no alignment rails. Tibial trialing assembly 310 includes broaching plate 312 and trialing plate 314. Broaching plate 312 includes an outer periphery shaped to conform to a resected tibia. The outer periphery includes anterior edge 316 and posterior edge 318. Broaching plate 312 also includes pin holes 330, which are adapted to receive fasteners (such as pins 36 in FIG. 4) for securing broaching plate 312 to the tibia. Broaching plate 312 also includes broach opening 332, which is sized and configured to allow the passage of a drill and/or broach. Broaching plate 312 also defines a pair of peg holes 334.

Figure 12:
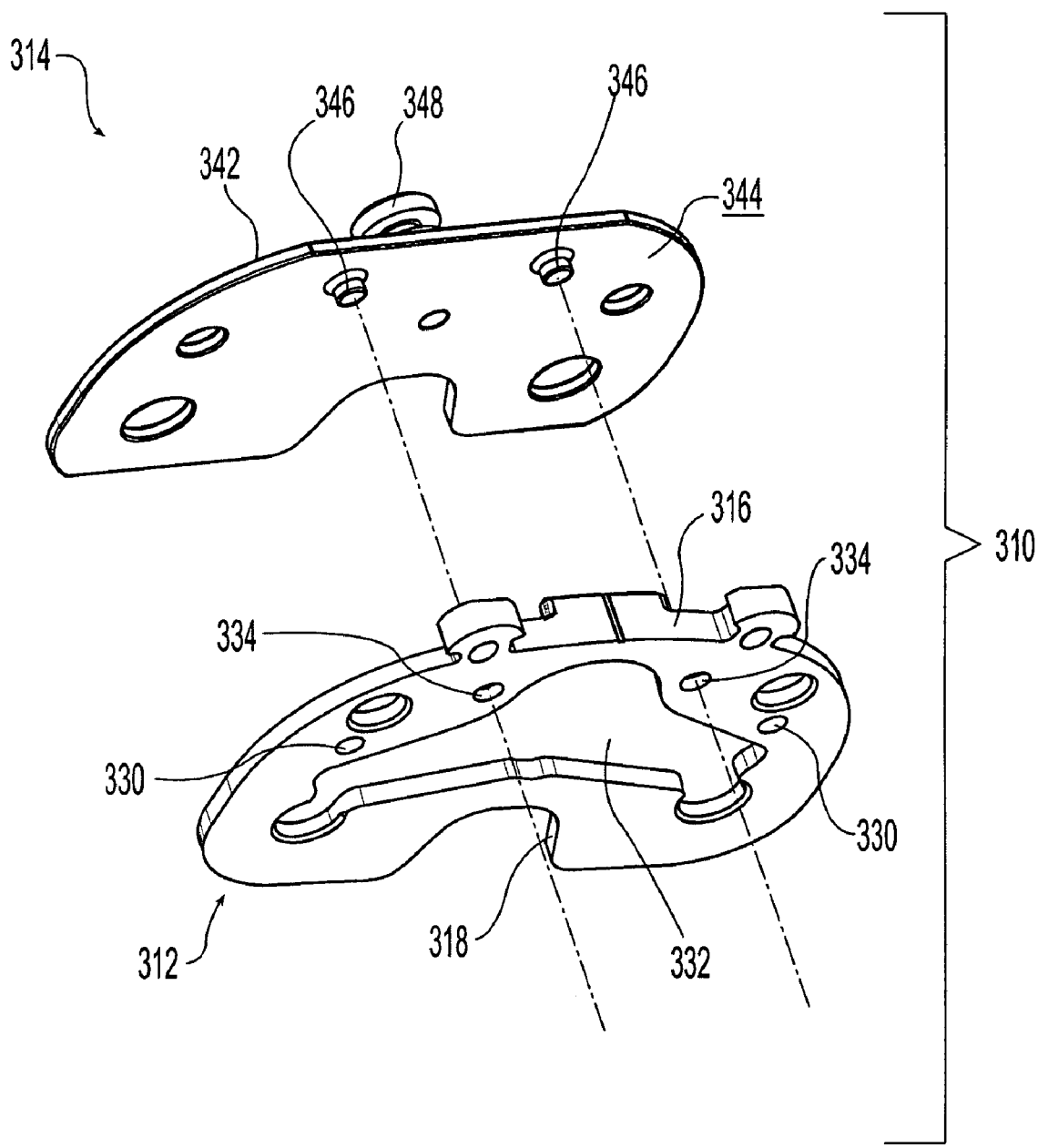
FIG. 12 is a perspective view of a disassembled tibial trialing assembly according to another embodiment of the present invention.
Figure 13:
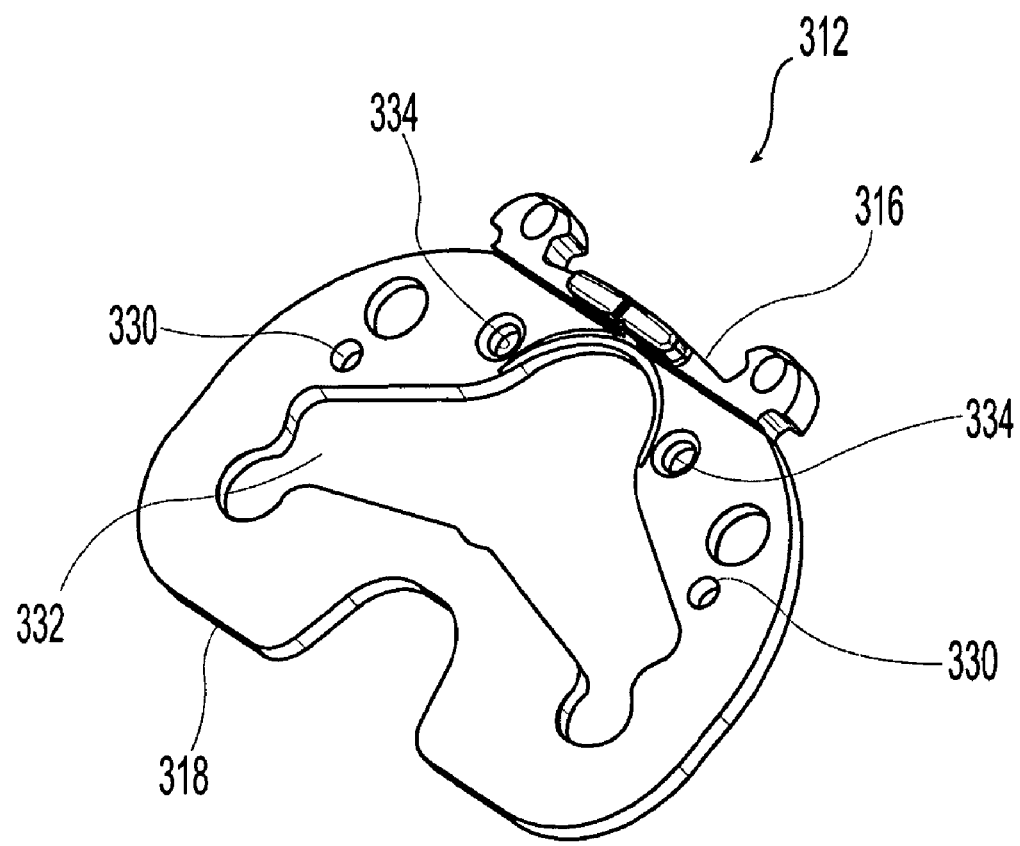
FIG. 13 is a perspective view of the broaching plate of the trialing assembly of FIG. 12.
Figure 14:
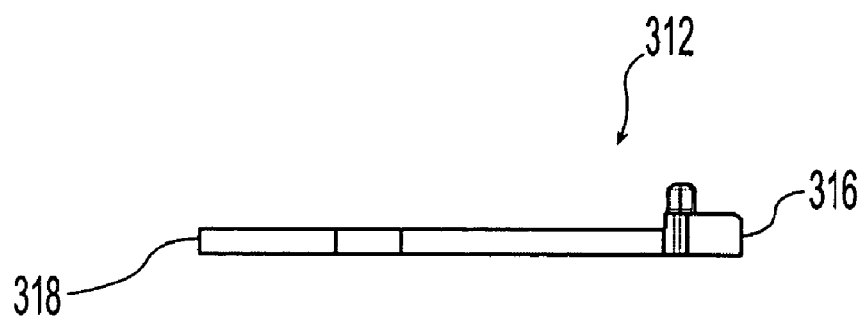
FIG. 14 is an end view of the broaching plate of FIG. 13.
Figure 15:
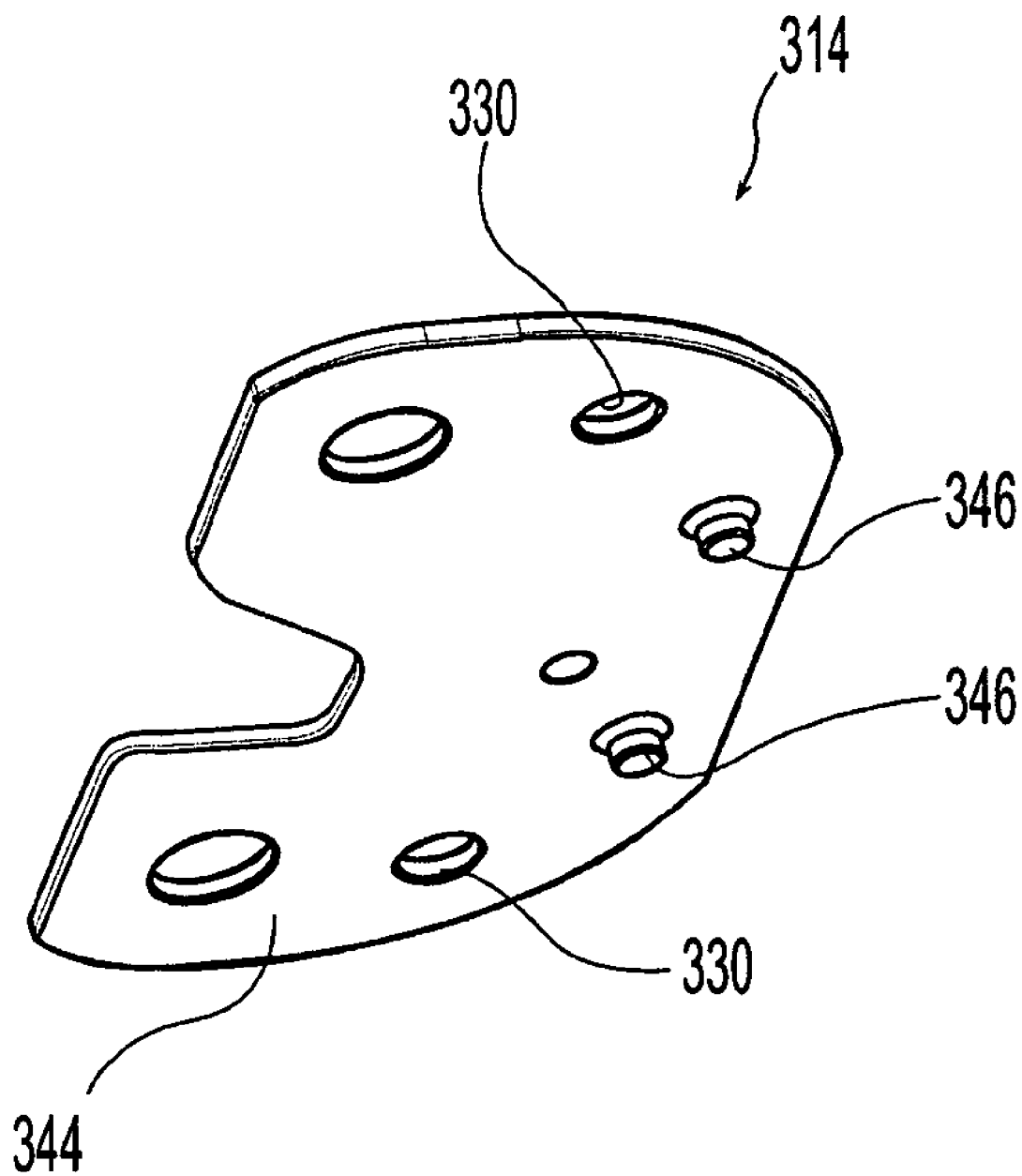
FIG. 15 is a perspective view of the trialing plate of the trialing assembly of FIG. 12.

Turning to FIGS. 12 and 15, trialing plate 314 is sized and configured to fit over broaching plate 312 and includes inferior surface 344 and opposing superior surface 342. Boss 348 protrudes superiorly from superior surface 342 and is adapted to engage with trialing surface provisionals. Trialing plate 314 also include pegs 346 extending from inferior surface 344. Pegs 346 are sized and positioned to align with and extend into peg holes 334 of broaching plate 312 when trialing plate 314 is seated on broaching plate 312. Pegs 346 serve to maintain trialing plate's 314 position atop broaching plate 312 and to prevent trialing plate 314 from sliding off of broaching plate 312. It should be understood that pegs 346 may be alternatively disposed on the top surface of broaching plate 312, while peg holes 334 may be alternatively disposed in the inferior surface of trialing plate 314.

Also, as shown in the embodiments described above, superior surface of the trialing plate is level with the superior surfaces of the rails. Alternatively, superior surface 42 of trialing plate 14 may be proud, or raised, with respect to superior surfaces 26a and 28a of anterior and posterior rails 26, 28 to provide a smooth surface and to prevent rails 26, 28 from interfering with the movement of the articular surface provisional.

Figure 16:
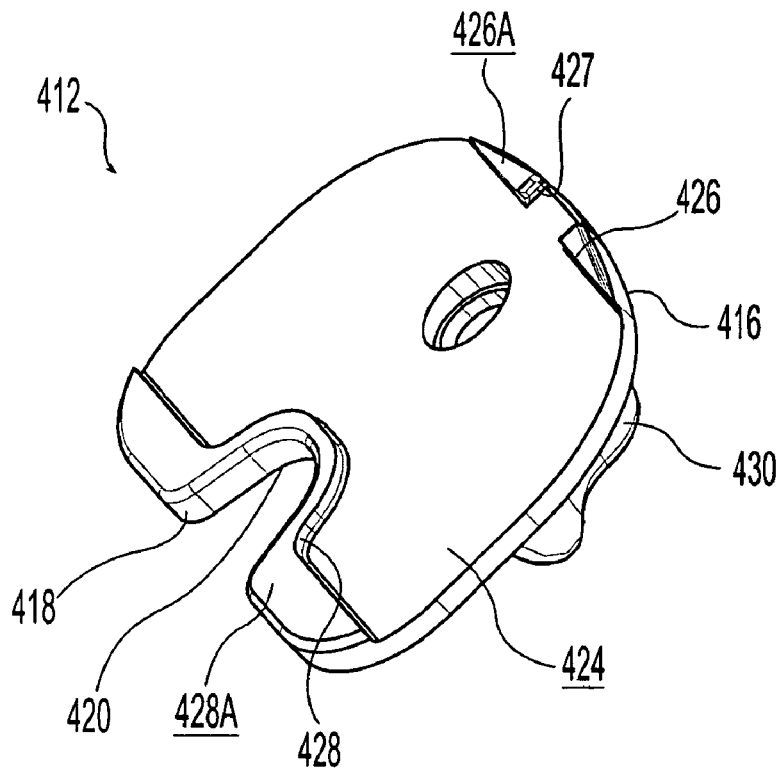
FIG. 16 is a perspective view of a provisional tibial base plate in accordance with one embodiment of the present invention.
Figure 17:
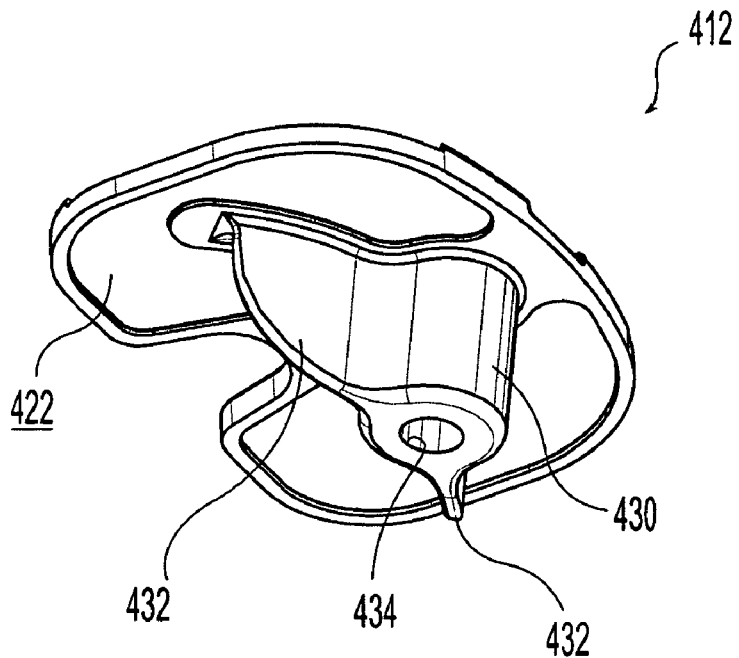
FIG. 17 is another perspective view of the provisional tibial base plate of FIG. 16.

Referring to FIGS. 16-19, provisional base plate 412 and complementary trialing plate 414 according to one embodiment of the present invention will now be described. Referring specifically to FIGS. 16 and 17, provisional base plate 412 according to the present invention is illustrated. Provisional base plate 412 is adapted to be mounted on the prepared end of the tibia after the passage has been drilled or broached into the tibia using a broaching plate as described above. Provisional base plate 412 includes anterior edge 416 and opposing posterior edge 418. Provisional base plate 412 also includes PCL cut out 420 at posterior edge 418. Provisional base plate includes opposing inferior and superior surfaces 422, and 424, respectively, which extend between anterior and posterior edges 416, 418. Pair of opposing alignment rails 426, 428 protrudes superiorly from superior surface 424. Pair of opposing alignment rails 426, 428 includes anterior rail 426, which extends along a portion of anterior edge 416, and posterior rail 428, which extends along a portion of posterior edge 418. Notch 427 is formed in anterior rail 426. Provisional base plate 412 also includes stem 430 extending inferiorly from inferior surface 422. Stem 430 is configured to be received in the passage, which was created in the tibia as described above. Stem 430 includes central bore 434 extending concentrically therein. Bore 434 may be configured to receive a stem extension (not shown) as needed. Alternatively, bore 434 may be threaded and adapted to receive an extraction tool, such as a threaded rod or handle, for extracting provisional base plate 412 from the tibia. Wings or flanges 432 extend radially outward from stem 430 and serve to aid in anchoring stem 430 in the passage in the tibia. Provisional base plate 412 may also be equipped with a magnet operable at superior surface 424 to hold trialing plate 414 in place atop provisional base plate 412.

Figure 18:
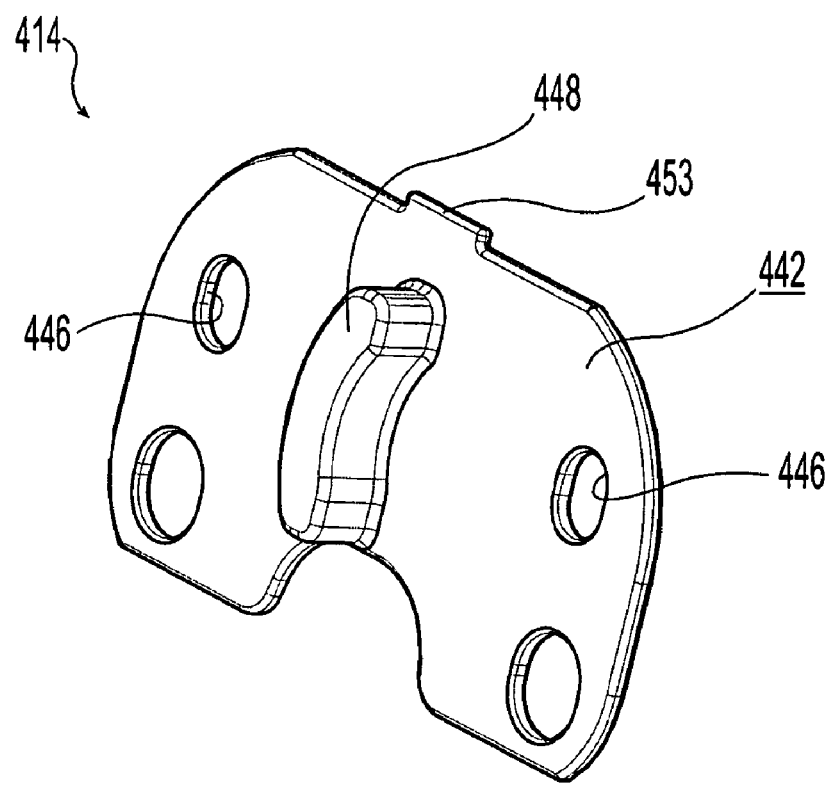
FIG. 18 is a perspective view of a trialing plate according to another embodiment of the present invention.
Figure 19:
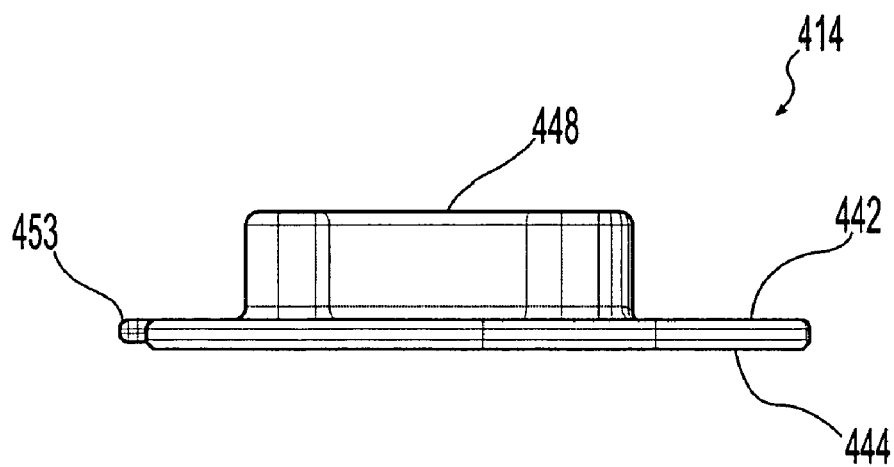
FIG. 19 is a side view of the trialing plate of FIG. 18.

Turning now to FIGS. 18 and 19, trialing plate 414 is illustrated. Trialing plate 414 includes superior surface 442 and opposing inferior surface 444. Head receiving openings 446 extend through trialing plate 414 from superior surface 442 to inferior surface 444. Boss 448 extends upwardly from superior surface 442 and, as suggested above, demonstrates yet another shape and size of the boss. As illustrated in FIG. 18, boss 448 is curved to provide limited arc of motion of the articular surface provisional (not shown) with which boss 448 mates. Accordingly, trialing plate 414 is configured to mimic the surface of a tibial base plate of a knee implant for use in the left knee. Alternatively, trialing plate 414 could be adapted to mimic the surface of a tibial base plate of right knee implant by providing a boss having a shape of a mirror-image to that of boss 448.

Tab 453 (FIG. 18) extends from an anterior edge of trialing plate 414 and is configured to mate with notch 427 of provisional base plate 412, shown in FIG. 16. Trialing plate 414 is substantially flat and is sized to fit over provisional base plate 412 between anterior and posterior rails 426, 428, such that superior surface 442 of trialing plate 414 is substantially level with superior surfaces 426A, 428A of corresponding anterior posterior rails 426, 428. When trialing plate 414 is positioned over provisional base plate 412, tab 453 is received in notch 427 to restrict movement of trialing plate 414 in the medial-lateral direction. Tab 453 also facilitates removal of the trialing plate from the broaching plate and provisional plate. Anterior and posterior rails 426, 428 prevent movement of trialing plate 414 in the anterior-posterior direction. Once trialing plate 414 is properly positioned atop provisional base plate, an articular surface provisional (not shown) may now be engaged with boss 448 and conventional trialing and sizing procedures may be performed.

Figure 20:
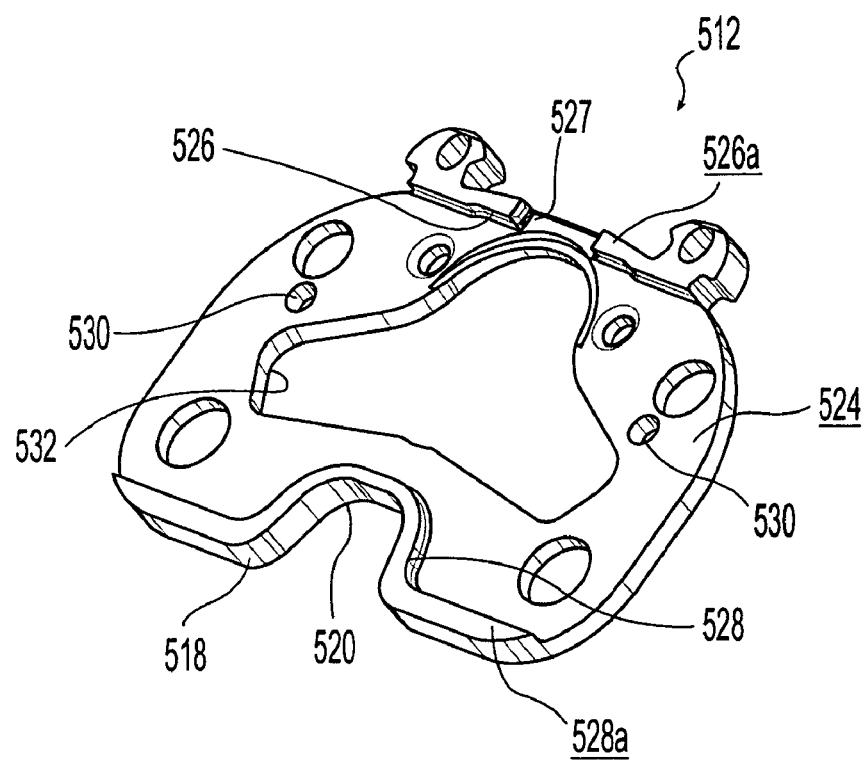
FIG. 20 is a top perspective view of a broaching plate according to another embodiment of the present invention.
Figure 21:
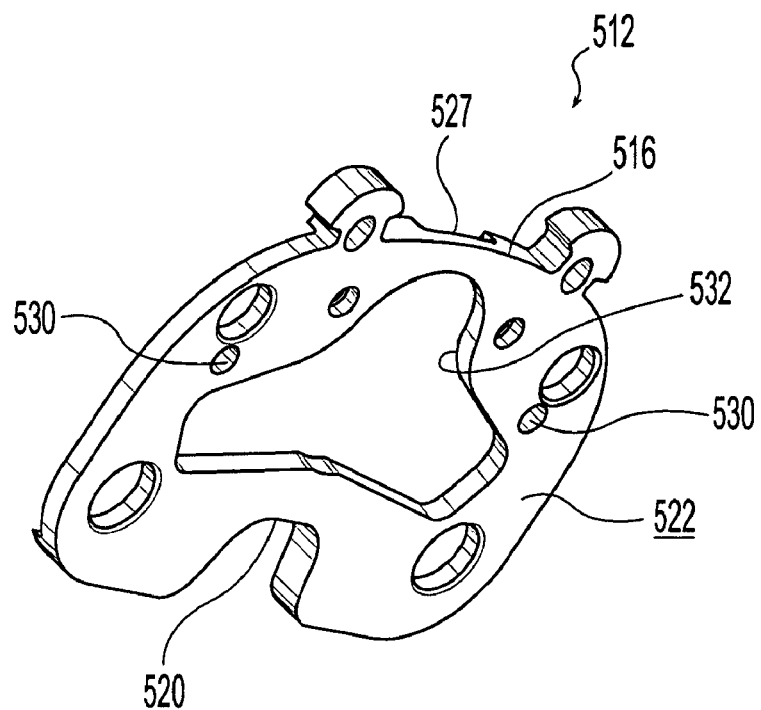
FIG. 21 is a bottom perspective view of the broaching plate of FIG. 20.

Trialing plate 414 is adapted to also mate with broaching plate 512, shown in FIGS. 20 and 21. Broaching plate 512 includes an outer periphery shaped to conform to a resected tibia. The outer periphery includes anterior edge 516 and opposing posterior edge 518. Broaching plate 512 also includes bottom surface 522 and opposing top surface 524. Bottom and top surfaces 522, 524 are substantially flat and extend between anterior edge 516 and posterior edge 518. Broaching plate 512 is sized for placement atop a resected tibia. Accordingly, bottom surface 522 is configured for placement on, and contact with, the resected tibia. In addition, a portion of posterior edge 518 curves inward toward anterior edge 516 to form PCL cutout 520. PCL cutout 520 is configured to accommodate the patient's posterior cruciate ligament when broaching plate 512 is placed atop the resected tibia.

Referring still to FIGS. 20 and 21, broaching plate 512 includes a pair of opposing alignment rails 526, 528 protruding superiorly from top surface 524. Pair of opposing alignment rails 526, 528 includes anterior rail 526, which extends along a portion of anterior edge 516, and posterior rail 528, which extends along a portion of posterior edge 518. Particularly, posterior rail 528 extends along and around PCL cutout 520 of posterior edge 518. Anterior rail 526 and posterior rail 528 include superior surfaces 526a, 528a, respectively. Pin holes 530 extend through broaching plate 512 from top surface 524 to bottom surface 522. Pin holes 530 are adapted to receive pins (such as pins 36 shown in FIG. 4) or any other fasteners including screws or nails, as further discussed below. Broaching plate 512 includes broach receiving opening 532 extending through broaching plate 512. Broach receiving opening 532 is sized and configured to allow the passage of a drill and/or a broach. Broaching plate also includes notch 527 formed in anterior rail 526.

Broaching plate 512 and trialing plate 414 are used in a manner similar to that described above with respect to broaching plate 12 and trialing plate 14. Broaching plate 512 is secured to the resected surface of the tibia by inserting pins through pin holes 530. Trialing plate 414 is placed over broaching plate 512 and is positioned between rails 526, 528 such that the heads of the pins are received in head receiving openings 446 of trialing plate 414 and tab 453 is positioned in notch 527. When so positioned, superior surface 442 of trialing plate 414 is level with superior surfaces 526a, 528a of anterior and posterior rails 526, 528. The assembly of broaching plate 512 and trialing plate 414 may be used to trial an articular surface provisional in a manner similar to that described above with respect to tibial trialing assembly 10.

Although the embodiments shown in the drawings and discussed above are used in the sizing and trialing of knee implants, it is contemplated that the present invention could be adapted for use in sizing and trialing other implants, including elbows and ankles.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A trialing assembly for use during a knee replacement procedure to prepare a resected tibia for receiving a tibial implant and to trial an articular surface provisional, said trialing assembly comprising:

a support plate having an outer periphery, said support plate including a bottom surface adapted for placement atop the resected tibia and an opposite top surface, said support plate having a posterior alignment rail, a medial anterior alignment rail, and a lateral anterior alignment rail, each of said posterior alignment rail, said medial anterior alignment rail, and said lateral anterior alignment rail extending from said top surface and positioned adjacent to said outer periphery of said support plate, said medial anterior alignment rail and said lateral anterior alignment rail spaced apart from one another to define a notch therebetween;

a trialing plate removably positionable on said top surface of said support plate between said posterior alignment rail, said medial anterior alignment rail, and said lateral anterior alignment rail, said trialing plate having a tab extending therefrom, said tab configured to be received within said notch defined by said medial anterior alignment rail and said lateral anterior alignment rail of said support plate, wherein interaction of said tab with said medial anterior alignment rail and said lateral anterior alignment rail substantially restricts medial-lateral movement of said trialing plate relative to said support plate; and a broaching plate having an inferior surface, a superior surface, an anterior broaching plate alignment rail, and a posterior broaching plate alignment rail, said trialing plate configured to be received between said anterior broaching plate alignment rail and said posterior broaching plate alignment rail, wherein said support plate comprises a base plate.

2. The trialing assembly of claim 1, wherein said trialing plate further comprises a provisional engagement member extending from a superior surface of said trialing plate, said provisional engagement member having an arcuate boss with a pair of opposing arcuate sides.

3. The trialing assembly of claim 1, wherein said broaching plate further comprises an anterior tab protruding anteriorly from said outer periphery thereof, said anterior tab having an opening extending therethrough.

4. The trialing assembly of claim 1, wherein said anterior broaching plate alignment rail comprises a medial anterior broaching plate alignment rail and a lateral anterior broaching plate alignment rail, said medial anterior broaching plate alignment rail and said lateral anterior broaching plate alignment rail separated from one another to define a broaching plate notch therebetween, said broaching plate notch sized to receive said tab of said trialing plate, wherein interaction of said tab of said trialing plate with said medial anterior broaching plate alignment rail and said lateral anterior broaching plate alignment rail substantially restricts movement of said trialing plate in a medial-lateral direction relative to said broaching plate.

5. The trialing assembly of claim 4, wherein said base plate further comprises a stem extending from said bottom surface, said trialing plate configured to be received between said medial anterior alignment rail, said lateral anterior alignment rail, and said posterior alignment rail, wherein interaction of said trialing plate with said medial anterior alignment rail, said lateral anterior alignment rail, and said posterior alignment rail substantially entirely prevents anterior-posterior movement of said trialing plate relative to said base plate.

6. The trialing assembly of claim 5, wherein said base plate further comprises a pair of flanges extending radially outwardly from said stem.

7. The trialing assembly of claim 5, wherein said trialing plate further comprises a provisional engagement member extending from a superior surface of said trialing plate, said provisional engagement member having an arcuate boss with a pair of opposing arcuate sides.

8. The trialing assembly of claim 5, wherein said broaching plate further comprises an anterior tab protruding anteriorly from said outer periphery thereof, said anterior tab having an opening extending therethrough.

9. The trialing assembly of claim 1, wherein said trialing plate further comprises a peg extending from an inferior surface thereof and said support plate includes an opening extending therethrough, said peg of said trialing plate sized for receipt within said opening of said support plate.

10. The trialing assembly of claim 1, wherein, with said trialing plate positioned on said top surface of said support plate, said trialing plate substantially entirely covers said top surface of said support plate.

11. A trialing assembly for use during a knee replacement procedure to prepare a resected tibia for receiving a tibial implant and to trial an articular surface provisional, said trialing assembly comprising:
a support plate having an outer periphery, said support plate including a bottom surface adapted for placement atop the resected tibia and an opposite top surface, said support plate having a posterior alignment rail, a medial anterior alignment rail, and a lateral anterior alignment rail, each of said posterior alignment rail, said medial anterior alignment rail, and said lateral anterior alignment rail extending from said top surface and positioned adjacent to said outer periphery of said support plate, said medial anterior alignment rail and said lateral anterior alignment rail spaced apart from one another to define a notch therebetween;
a trialing plate removably positionable on said top surface of said support plate between said posterior alignment rail, said medial anterior alignment rail, and said lateral anterior alignment rail, said trialing plate having a tab extending therefrom, said tab configured to be received within said notch defined by said medial anterior alignment rail and said lateral anterior alignment rail of said support plate, wherein interaction of said tab with said medial anterior alignment rail and said lateral anterior alignment rail substantially restricts medial-lateral movement of said trialing plate relative to said support plate; and
a provisional base plate having an inferior surface, a superior surface, an anterior base plate alignment rail, a posterior base plate alignment rail, and a stem extending from said inferior surface, said trialing plate configured to be received between said anterior base plate alignment rail and said posterior base plate alignment rail, wherein interaction of said trialing plate with said anterior base plate alignment rail and said posterior base plate alignment rail substantially entirely prevents anterior-posterior movement of said trialing plate relative to said provisional base plate,
wherein said support plate comprises a broaching plate.

12. The trialing assembly of claim 11, wherein said provisional base plate further comprises a pair of flanges extending radially outwardly from said stem.

13. The trialing assembly of claim 11, wherein said anterior base plate alignment rail comprises a medial anterior base plate alignment rail and a lateral anterior base plate alignment rail, said medial anterior base plate alignment rail and said lateral anterior base plate alignment rail separated from one another to define a base plate notch therebetween, said base plate notch sized to receive said tab of said trialing plate, wherein interaction of said tab of said trialing plate with said medial anterior base plate alignment rail and said lateral anterior base plate alignment rail substantially restricts movement of said trialing plate in a medial-lateral direction relative to said base plate.

14. The trialing assembly of claim 11, wherein said trialing plate further comprises a provisional engagement member extending from a superior surface of said trialing plate, said provisional engagement member having an arcuate boss with a pair of opposing arcuate sides.

15. The trialing assembly of claim 11, wherein said broaching plate further comprises an anterior tab protruding anteriorly from said outer periphery thereof, said anterior tab having an opening extending therethrough.

16. The trialing assembly of claim 11, wherein said trialing plate further comprises a peg extending from an inferior surface thereof and said support plate includes an opening extending therethrough, said peg of said trialing plate sized for receipt within said opening of said support plate.

17. The trialing assembly of claim 11, wherein, with said trialing plate positioned on said top surface of said support plate, said trialing plate substantially entirely covers said top surface of said support plate.

18. A trialing assembly for use during a knee replacement procedure to prepare a resected tibia for receiving a tibial implant and to trial an articular surface provisional, said trialing assembly comprising:
a support plate having an outer periphery, said support plate including a bottom surface adapted for placement atop the resected tibia and an opposite top surface, said support plate having a posterior alignment rail and an anterior alignment rail, said posterior alignment rail and said anterior alignment rail defining at least a portion of said outer periphery of said support plate, said top surface of said support plate extending between said posterior alignment rail and said anterior alignment rail;
a trialing plate removably positionable on said top surface of said support plate between said posterior alignment rail and said anterior alignment rail, wherein interaction of said trialing plate with said posterior alignment rail and said anterior alignment rail substantially entirely prevents anterior-posterior movement of said trialing plate relative to said support plate; and
a broaching plate having an inferior surface, a superior surface, an anterior broaching plate alignment rail, and a posterior broaching plate alignment rail, said trialing plate configured to be received between said anterior broaching plate alignment rail and said posterior broaching plate alignment rail,
wherein said support plate comprises a base plate.

19. The trialing assembly of claim 18, wherein said anterior alignment rail of said support plate further comprises a medial anterior alignment rail and a lateral anterior alignment rail and said trialing plate further comprises a tab, said medial anterior alignment rail spaced from said lateral anterior alignment rail to define a notch therebetween, said tab sized for receipt within said notch, wherein interaction of said tab with said medial anterior alignment rail and said lateral anterior alignment rail substantially restricts medial-lateral movement of said trialing plate relative to said support plate.

20. The trialing assembly of claim 18, wherein said trialing plate further comprises a provisional engagement member extending from a superior surface of said trialing plate, said provisional engagement member having an arcuate boss with a pair of opposing arcuate sides.

21. The trialing assembly of claim 18, wherein said broaching plate further comprises an anterior tab protruding anteriorly from said outer periphery thereof, said anterior tab having an opening extending therethrough.

22. The trialing assembly of claim 18, wherein said trialing plate further comprises a peg extending from an inferior surface thereof and said support plate includes an opening extending therethrough, said peg of said trialing plate sized for receipt within said opening of said support plate.

23. The trialing assembly of claim 18, wherein, with said trialing plate positioned on said top surface of said support plate, said trialing plate substantially entirely covers said top surface of said support plate.

24. The trialing assembly of claim 18, wherein said base plate further comprises a stem extending from said bottom surface, said trialing plate configured to be received between said anterior alignment rail and said posterior alignment rail, wherein interaction of said trialing plate with said anterior alignment rail and said posterior alignment rail substantially entirely prevents anterior-posterior movement of said trialing plate relative to said base plate.

25. A trialing assembly for use during a knee replacement procedure to prepare a resected tibia for receiving a tibial implant and to trial an articular surface provisional, said trialing assembly comprising:
  a support plate having an outer periphery, said support plate including a bottom surface adapted for placement atop the resected tibia and an opposite top surface, said support plate having a posterior alignment rail and an anterior alignment rail, said posterior alignment rail and said anterior alignment rail defining at least a portion of said outer periphery of said support plate, said top surface of said support plate extending between said posterior alignment rail and said anterior alignment rail;
  a trialing plate removably positionable on said top surface of said support plate between said posterior alignment rail and said anterior alignment rail, wherein interaction of said trialing plate with said posterior alignment rail and said anterior alignment rail substantially entirely prevents anterior-posterior movement of said trialing plate relative to said support plate; and
  a provisional base plate having an inferior surface, a superior surface, an anterior base plate alignment rail, a posterior base plate alignment rail, and a stem extending from said inferior surface, said trialing plate configured to be received between said anterior base plate alignment rail and said posterior base plate alignment rail, wherein interaction of said trialing plate with said anterior base plate alignment rail and said posterior base plate alignment rail substantially entirely prevents anterior-posterior movement of said trialing plate relative to said provisional base plate,
  wherein said support plate comprises a broaching plate.

26. The trialing assembly of claim 25, wherein said provisional base plate further comprises a pair of flanges extending radially outwardly from said stem.

27. The trialing assembly of claim 25, wherein said anterior alignment rail of said support plate further comprises a medial anterior alignment rail and a lateral anterior alignment rail and said trialing plate further comprises a tab, said medial anterior alignment rail spaced from said lateral anterior alignment rail to define a notch therebetween, said tab sized for receipt within said notch, wherein interaction of said tab with said medial anterior alignment rail and said lateral anterior alignment rail substantially restricts medial-lateral movement of said trialing plate relative to said support plate.

28. The trialing assembly of claim 25, wherein said trialing plate further comprises a provisional engagement member extending from a superior surface of said trialing plate, said provisional engagement member having an arcuate boss with a pair of opposing arcuate sides.

29. The trialing assembly of claim 25, wherein said broaching plate further comprises an anterior tab protruding anteriorly from said outer periphery thereof, said anterior tab having an opening extending therethrough.

30. The trialing assembly of claim 25, wherein said trialing plate further comprises a peg extending from an inferior surface thereof and said support plate includes an opening extending therethrough, said peg of said trialing plate sized for receipt within said opening of said support plate.

31. The trialing assembly of claim 25, wherein, with said trialing plate positioned on said top surface of said support plate, said trialing plate substantially entirely covers said top surface of said support plate.

* * * * *